United States Patent [19]
Kim et al.

[11] Patent Number: 6,127,575
[45] Date of Patent: Oct. 3, 2000

[54] PROCESS FOR PREPARING N,N'-DISUBSTITUTED UREA USING SELENIUM-BASED CATALYST

[75] Inventors: Hoon Sik Kim; Yong Jin Kim; Hyun Joo Lee; Moon Jo Chung; Sang Deuk Lee, all of Seoul, Rep. of Korea

[73] Assignee: Korea Institute of Science and Technology, Seoul, Rep. of Korea

[21] Appl. No.: 09/395,388

[22] Filed: Sep. 13, 1999

[30] Foreign Application Priority Data

Sep. 18, 1998 [KR] Rep. of Korea ............ 98/38729

[51] Int. Cl.$^7$ .................................... C07C 273/00
[52] U.S. Cl. .................. 564/47; 564/57; 564/58; 564/67
[58] Field of Search .................. 564/58, 57, 47, 564/67

[56] References Cited

U.S. PATENT DOCUMENTS 4,052,454 10/1977 Zajacek et al. .

FOREIGN PATENT DOCUMENTS 0 319 111 A2 11/1988 European Pat. Off. .
62-59253 3/1987 Japan .

OTHER PUBLICATIONS

Kiyoshi, Kondo, et al., "A New Synthesis of Carbamates, The Reaction of Carbon Monoxide With Amine and Alcohol In the Co–Presence of Selenium and Triethylamine", Published by The Chemical Society of Japan, Chemistry Letters, pp. 373–374 (1961).

R.A. Franz, et al.; "A New Synthesis of Ureas, III, The Reaction of Aromatic Amines with Carbon Monoxide and Sulfur", J. Org. Chem, pp. 3309–3319, 3303, (1961).

*Primary Examiner*—Paul J. Killos
*Attorney, Agent, or Firm*—Darby & Darby

[57] ABSTRACT

A process is disclosed for preparing N,N'-disubstituted urea by reacting an amine and $CO/O_2$ mixture gas in the presence of a catalyst system comprising at least one selenium compound selected from $SeO_2$, $(CH_3O)Se(O)(OH)$ and $(CH_3CH_2O)Se(O)(OH)$, and $M_2CO_3$ (M=alkali metal) as a co-catalyst. The process enables less active aromatic amine with a low reactivity as well as an aliphatic amine to be easily transformed into disubstituted urea avoiding the use of expensive precious metal catalysts.

11 Claims, No Drawings

PROCESS FOR PREPARING N,N'-DISUBSTITUTED UREA USING SELENIUM-BASED CATALYST

BACKGROUND OF THE INVENTION

1. Field of the Invention

The present invention relates to a process for preparing N,N'-disubstituted urea which is useful for agricultural chemicals, herbicides, pesticides and carbamates.

More particularly, the present invention relates to an improved process for preparing disubstituted urea by reacting an amine with a mixture of carbon monoxide and oxygen in the presence of a catalyst composition consisting of at least one selenium compound as a main catalyst and an alkali metal carbonate as a co-catalyst.

2. Description of the Prior Art

The conventional process for preparing N,N'-disubstituted urea from amine and phosgene has disadvantages in that phosgene is a lethal and highly corrosive compound, and the method generates much HCl, a known pollutant.

R. A. Franz, J. Org. CHEM., vol 26, p3309 (1961) teaches a process for preparing urea by reacting an amine with CO and S in the presence of a tertiary amine as a catalyst, but by using sulfur, the process generates by-products, such as $H_2S$ which is difficult to treat.

Japanese Patent Publication No. Sho 62-59,253 discloses a method for preparing urea from nitro compounds in the presence of catalysts such as rhodium and ruthenium at a relatively high turnover rate and selectivity. However, such catalysts of expensive precious metals may be disadvantageously decomposed at a high temperature and high reaction pressure.

Koyochi Kondo, Chemistry Letter, p373(1972) discloses a process of preparing urea by carbonylating an amine in the presence of a selenium catalyst. However, since the process uses an equivalent amount of selenium, a significant catalyst loss occurs. Furthermore, the reaction does not proceed when an aromatic amine is used as a starting material.

U.S. Pat. No. 4,052,454 discloses a process for preparing urea by reacting nitro compounds with water and CO in the presence of a selenium catalyst. However, as disclosed in its first embodiment, the process suffers from certain disadvantages, i.e., it is non-economical. Namely, when the reaction proceeds at about ⅛ molar fraction of catalyst to nitrobenzene as starting materials at 150° C. and 53 atm, the conversion of nitrobenzene and yield of the urea are 66.3% and 33.8%, respectively (turnover number, defined as molar urea produced per unit time and unit molar catalyst, <2).

European Patent No. 0 319,111 teaches a process for preparing urea from an amine and nitrobenzene wherein the activity of a palladium catalyst is maintained by adding redox agents, such as copper, manganese, vanadium, and chromium. However, as disclosed in its first embodiment, when the reaction proceeds at 140° C. and 50 atm for 20 hours, the maximum yield of 1,1-dimethyl-3-(4-chlorobenzene) urea is very low, i.e., 73% (turnover number <4).

As described above, the conventional processes for preparing urea are insufficient for industrial purposes. Furthermore, when an aromatic amine is singly employed, the yield of urea is extremely low.

SUMMARY OF THE INVENTION

An object of the present invention is to overcome the disadvantages of the known processes for preparing urea by providing a process for preparing N,N'-disubstituted urea at a high yield without any of the problems known in the conventional art, by using a new catalyst composition. The new catalyst composition consists essentially of a selenium compound as a main catalyst and an alkali metal carbonate compound as a co-catalyst.

It is another object of the present invention to provide a process to produce an efficient catalyst system comprising a selenium compound and an alkali metal carbonate compound for the production of N,N'-disubstituted urea with high yield and selectivity.

It is another object of the present invention to provide an improved process for preparing urea and to reduce the necessary amount of catalyst by using a selenium and alkali metal carbonate catalyst system. Namely, the conventional art requires a severe reaction condition, which causes loss of the catalyst, while the process according to the present invention prevents the loss of catalyst by operating the reaction at a relatively mild condition in the presence of an active selenium-based catalyst.

Also, it is another object of the present invention to provide a process for preparing N,N'-disubstituted aromatic urea in high yield from an less active aromatic amine by using a catalyst system consisting essentially of a selenium compound and alkali metal carbonate compound.

To achieve the above-described objects, the present invention provides an improved process for preparing a N,N'-disubstituted urea of the following chemical formula A, wherein an amine is reacted with a $CO/O_2$ mixture gas in a solvent in the presence of a catalyst system comprising at least one selenium compound selected from a group consisting of $SeO_2$, $(CH_3O)Se(O)(OH)$ and $(CH_3CH_2O)Se(O)(OH)$ as a main catalyst and an alkali metal carbonate compound as co-catalyst:

$$(RNH)_2CO \qquad (A)$$

wherein, R is an alkyl group of $C_1$–$C_{18}$, a cyclohexyl group, a phenyl group or a benzyl group.

The objects and advantages of the present invention will become more readily apparent from the detailed description given below. However, it should be understood that the detailed description and specific examples, while indicating preferred embodiments of the present invention, are given by way of illustration only, since various changes and modifications within the spirit and scope of the invention will become apparent to those skilled in the art for the detailed description.

DETAILED DESCRIPTION OF THE PREFERRED EMBODIMENTS

The present invention relates to a process for preparing N,N'-disubstituted urea by reacting an amine with a $CO/O_2$ gas mixture in the presence of a catalyst system consisting essentially of a selenium compound as a main catalyst and an alkali metal carbonate compound of the chemical formula, $M_2CO_3$ (M=alkali metal) as a co-catalyst.

Surprisingly, the inventors of the present invention have found that a N,N'-disubstituted urea can be prepared in a high yield from an aromatic compound as well as from an aliphatic amine in the presence of a catalyst system which comprises at least a selenium compound as a main catalyst and an alkali metal carbonate compound as a promoter. The selenium compound is selected from the group consisting of $SeO_2$, $(CH_3O)Se(O)(OH)$, and $(CH_3CH_2O)Se(O)(OH)$. Therefore, as indicated in the following reaction formula (I), a disubstituted urea can be produced in a high yield from an aromatic amine compound which is inactive in the presence of the selenium catalyst alone. In addition, the present method requires a much lower amount of a selenium compound as a catalyst, compared with the conventional processes.

$$2RNH_2 + CO + \tfrac{1}{2}O_2 \rightarrow (RNH)_2CO + H_2O \qquad (I)$$

The catalyst system comprising at least a selenium compound and an alkali metal carbonate is inexpensive and has a high catalytic activity, and thus can advantageously replace expensive precious metals such as Pd, Pt, Rh, etc.

The preparation of urea according to the present invention is characterized in that an amine is reacted with carbon monoxide and oxygen in a liquid phase and in the presence of a catalyst system comprising at least a selenium compound and an alkali metal carbonate.

According to the present invention, the reaction may proceed without solvent. However, it is preferable to use a solvent in the method in the aspects of agitation, separation of the catalyst and the efficiency of the reaction. Alcohol of $C_{1-3}$ or polar solvents such as THF, DMF, DMSO, and α,α,α-trifluorobenzene can be employed as solvents. Considering the reactivity and separation problems in the subsequent steps, it is more preferable to use an alcohol of C1–C3, for example, methanol, ethanol, n-propanol or isopropanol.

The amine group used in the present invention includes aliphatic amines such as methyl amine, ethyl amine, isopropyl amine, butylamine, isobutylamine, hexyl amine, dodecyl amine, hexaldecyl amine, and octadecyl amine; aromatic amines such as benzyl amine, and phenyl amine; and cycloalkyl amines such as cyclobutyl amine, and cyclohexyl amine.

The selenium compounds employed as a catalyst in the present invention are at least one selected from the group consisting of $SeO_2$, $(CH_3O)Se(O)(OH)$ and $(CH_3CH_2O)Se(O)(OH)$, and the molar ratio of catalyst to amine can be varied in the range of 1:12800–1:200, and preferably 1:3200–1:400. When the molar ratio is less than 1:12800, the rate of reaction is extremely low, and when the molar ratio is greater than 1:200, a large portion of the catalyst is disadvantageously consumed.

The alkali metal carbonate may be used as a co-catalyst in the present invention. The amount of the alkali metal carbonate used (for example, $Li_2CO_3$, $Na_2CO_3$, $K_2CO_3$, $Rb_2CO_3$, or $Cs_2CO_3$) is 0.1–10 times (mol/mol) that of the selenium compound used as a main catalyst, preferably 0.5–5 times (mol/mol). If it is less than 0.1 times (mol/mol), the reaction will be very slow and if it is more than 10 times, it is not economical because the amount of alkali metal carbonate used is more than the needed amount.

The temperature at which the reaction is carried out is within 80–250° C., depending upon the amine employed. In consideration of the reaction speed and selectivity to urea, the temperature is preferably between 100 and 140° C.

The pressure at which the reaction is carried out is usually between 3 and 200 atm, again depending upon the amine group employed.

The molar ratio of CO to $O_2$ used for the reaction is preferably in the range from 95:5 to 55:45, in consideration of the reactivity and explosion limit of the mixed gas.

With reference to the following examples, the present invention will now be described but the scope of the invention is not limited to the examples given herein.

EXAMPLE 1

A 300 ml high pressure stainless steel Parr bomb with an agitator was loaded with aniline (29.76 g, 320 mmol), $CH_3OH$ 25 cc, $SeO_2$ (22 mg, 0.2 mmol) and $K_2CO_3$ (69 mg, 0.5 mmol), and reacted with a $CO/O_2$ mixture ($CO/O_2$=90/10) at a temperature of 120° C. and 70 atm for one hour. After the reaction, the bomb was cooled to room temperature.

The product mixtures were analyzed by gas chromatography and HPLC. 95.2% conversion of aniline resulted with 87.5% yield of purified diphenylurea.

The conversion of aniline and the yield of diphenylurea were calculated as follows:

$$\text{aniline conversion (\%)} = \frac{\text{moles of aniline reacted}}{\text{moles of aniline employed}} \times 100$$

$$\text{urea yield} = \frac{2 \times \text{moles of urea produced}}{\text{moles of aniline employed}}$$

EXAMPLES 2–11

Experiments were carried out under the same conditions as in Example 1, except for the selenium compound and promoter. The results are shown in Table 1, wherein 0.1 mmol of the catalyst mixture was respectively used.

TABLE 1

| | Catalysts | $M_2CO_3$ | Aniline Conversion (%) | Diphenyl urea Yield (%) |
|---|---|---|---|---|
| Ex. 2 | $SeO_2$ | $Li_2CO_3$ | 68.7 | 66.7 |
| Ex. 3 | $SeO_2$ | $Na_2CO_3$ | 83.5 | 79.6 |
| Ex. 4 | $SeO_2$ | $Rb_2CO_3$ | 97.3 | 90.8 |
| Ex. 5 | $SeO_2$ | $Cs_2CO_3$ | 98.1 | 91.7 |
| Ex. 6 | $(CH_3OH)Se(O)(OH)$ | $K_2CO_3$ | 93.9 | 90.6 |
| Ex. 7 | $(CH_3OH)Se(O)(OH)$ | $Cs_2CO_3$ | 97.4 | 92.1 |
| Ex. 8 | $(CH_3CH_2O)Se(O)(OH)$ | $K_2CO_3$ | 94.1 | 89.5 |
| Ex. 9 | $(CH_3CH_2O)Se(O)(OH)$ | $Cs_2CO_3$ | 96.9 | 91.4 |
| Ex. 10 | $SeO_2/(CH_3)Se(O)(OH)$ | $K_2CO_3$ | 97.8 | 90.6 |
| Ex. 11 | $SeO_2/(CH_3CH_2O)Se(O)(OH)$ | $Cs_2CO_3$ | 97.9 | 89.9 |

(wherein, M is alkali metal)

EXAMPLES 12–17

The procedure of example 1 was repeated except that the experiments were carried out by varying the molar ratio of anilines to $SeO_2$. The molar ration of $SeO_2$ and $K_2CO_3$ was fixed and the results are shown in Table 2.

TABLE 2

| | Molar ratio (Aniline/$SeO_2$) | Conversion (%) | Yield (%) |
|---|---|---|---|
| Ex. 12 | 12800 | 32.8 | 32.6 |
| Ex. 13 | 6400 | 50.2 | 49.5 |
| Ex. 14 | 3200 | 66.1 | 63.4 |
| Ex. 15 | 800 | 96.1 | 77.5 |
| Ex. 16 | 400 | 95.2 | 72.6 |
| Ex. 17 | 200 | 96.3 | 70.9 |

EXAMPLES 18–23

Experiments were carried out under the same condition as in Example 1, except for changing the amounts of $K_2CO_3$. The results are shown in Table 3.

TABLE 3

|  | $K_2CO_3/SeO_2$ | Conversion (%) | Yield (%) |
| --- | --- | --- | --- |
| Ex. 18 | 0.1 | 17.3 | 17.2 |
| Ex. 19 | 0.5 | 36.6 | 34.9 |
| Ex. 20 | 1 | 79.8 | 79.1 |
| Ex. 21 | 5 | 95.8 | 85.6 |
| Ex. 22 | 7 | 96.9 | 83.2 |
| Ex. 23 | 10 | 94.7 | 81.9 |

EXAMPLES 24–28

Experiments were carried out while changing the temperature, pressure and $CO/O_2$ molar fraction, and the results are shown in Table 4.

TABLE 4

|  | Temp (° C.) | P (atm) | $CO/O_2$ | Conversion (%) | Yield (%) |
| --- | --- | --- | --- | --- | --- |
| Ex. 24 | 80 | 200 | 55/45 | 15.3 | 15.3 |
| Ex. 25 | 120 | 100 | 70/30 | 94.9 | 84.6 |
| Ex. 26 | 150 | 60 | 80/20 | 95.8 | 69.5 |
| Ex. 27 | 200 | 50 | 90/10 | 96.8 | 23.1 |
| Ex. 28 | 250 | 30 | 95/5 | 97.4 | 17.6 |

EXAMPLES 29–35

Experiments were carried out under the same conditions as in Example 1, while changing the amine substrate and alcohol solvent. The results are shown in Table 5.

TABLE 5

|  | Amine | Alcohol | Amine conversion (%) | Urea Yield (%) |
| --- | --- | --- | --- | --- |
| Ex. 29 | Butyl amine | Methanol | 99.9 | 84.4 |
| Ex. 30 | Cyclohexyl amine | Methanol | 99.8 | 89.6 |
| Ex. 31 | Aniline | Ethanol | 94.8 | 85.4 |
| Ex. 32 | Benzyl amine | i-propanol | 93.7 | 76.5 |
| Ex. 33 | 2-methy aniline | Methanol | 84.7 | 84.1 |
| Ex. 34 | 2,4-dimethyl aniline | Methanol | 96.3 | 94.8 |
| Ex. 35 | 2,4,6-trimethyl aniline | Methanol | 96.0 | 95.4 |

As described above, the present invention provides a process for preparing N,N'-disubstituted urea from an aromatic amine in the presence of a new catalyst system comprising a selenium compound and an alkali metal carbonate. The use of a highly active and less expensive selenium-based catalyst enables the above process to be much more economical compared with the conventional processes which employ expensive precious metal catalysts.

As the present invention may be embodied in several forms without departing from the spirit of the essential characteristics thereof, it should also be understood that the above-described embodiments are not limited by any of the details of the foregoing description, unless otherwise specified, but rather the present invention should be construed broadly within its spirit and scope as defined in the appended claims, and therefore all changes and modifications that fall within the metes and bounds of the claims, or equivalences of such metes and bounds are therefore intended to be embraced by the appended claims.

What is claimed is:

1. A process for preparing a N,N'-disubstituted urea of the following chemical formula I by reacting an amine with a $CO/O_2$ mixture gas in a solvent and in the presence of a catalyst system comprising at least one selenium compound selected from the group consisting of $SeO_2$, $(CH_3O)Se(O)(OH)$ and $(CH_3CH_2O)Se(O)(OH)$ as a main catalyst component and an alkali metal carbonate as a co-catalyst:

$$(RNH)_2CO \qquad (I)$$

wherein, R is an alkyl group of $C_1$–$C_{18}$, a cyclohexyl group, a phenyl group or a benzyl group.

2. The process of claim 1, wherein the alkali metal carbonate is one selected from the group consisting of $Li_2CO$, $Na_2CO_3$, $K_2CO_3$, $Rb_2CO_3$ and $Cs_2CO_3$.

3. The process of claim 1, wherein the molar ratio of the selenium compound to amine compound ranges from 1/12800 to 1/200 (mol/mol).

4. The process of claim 3, wherein the molar ratio of the selenium compound to amine compound ranges from 1/3200 to 1/400 (mol/mol).

5. The process of claim 1, wherein the molar fraction of the alkali metal carbonate to selenium compound ranges from 0.1 to 10 (mol/mol).

6. The process of claim 5, wherein the molar ratio of alkali metal carbonate to selenium compound ranges from 0.5 to 5 (mol/mol).

7. The process of claim 1, wherein the amine group is one selected from the group consisting of methylamine, ethyl amine, isopropyl amine, butyl amine, isobutyl amine, heel amine, dodecyl amine, hexaldecyl amine, octadecyl amine, benzyl amine, phenyl amine, cyclobutyl amine, and cyclohexyl amine.

8. The process of claim 1, wherein the solvent is one selected from the group consisting of methanol, ethanol, n-propanol and isopropanol.

9. The process of claim 1, wherein the reaction is carried out at a temperature of 80 to 250° C., and at a pressure of 30 to 200 atm.

10. The process of claim 9, wherein the reaction is carried out at a temperature of 100 to 140° C., and at a pressure of 50 to 100 atm.

11. The process of claim 1, wherein the molar ratio of CO to $O_2$ ranges from 95:5 to 55:45 (mol/mol).

* * * * *